US008789156B2

(12) United States Patent
Fisk et al.

(10) Patent No.: US 8,789,156 B2
(45) Date of Patent: Jul. 22, 2014

(54) DATA MANAGEMENT WITH A NETWORKED MOBILE DEVICE

(75) Inventors: Frank C. Fisk, Lawrenceville, GA (US); Sri Ramanathan, Lutz, FL (US); Matthew A. Terry, Dunwoody, GA (US); Matthew B. Trevathan, Kennesaw, GA (US)

(73) Assignee: International Business Machines Corporation, Armonk, NY (US)

( * ) Notice: Subject to any disclaimer, the term of this patent is extended or adjusted under 35 U.S.C. 154(b) by 164 days.

(21) Appl. No.: 13/213,261

(22) Filed: Aug. 19, 2011

(65) Prior Publication Data

US 2013/0047233 A1 Feb. 21, 2013

(51) Int. Cl.
*G06F 7/04* (2006.01)
*G06F 21/60* (2013.01)
*G06F 21/30* (2013.01)
*G06F 21/62* (2013.01)
*H04L 29/06* (2006.01)

(52) U.S. Cl.
CPC .............. *G06F 21/606* (2013.01); *G06F 21/30* (2013.01); *G06F 21/6245* (2013.01); *H04L 63/0492* (2013.01)
USPC ......................... 726/7; 726/6; 726/4; 713/156

(58) Field of Classification Search
CPC ....... G06F 21/606; G06F 21/31; G06F 21/30; G06F 21/6245; G06F 2221/2141; H04L 63/0492; H04L 9/3234
See application file for complete search history.

(56) References Cited

U.S. PATENT DOCUMENTS

| 7,127,300 B2 * | 10/2006 | Mazar et al. ................ 607/60 |
| 7,552,862 B2 | 6/2009 | Flake et al. |
| 2007/0111726 A1 | 5/2007 | Lambert et al. |
| 2008/0046978 A1 * | 2/2008 | Rieger .............................. 726/4 |
| 2008/0189768 A1 * | 8/2008 | Callahan et al. ................ 726/4 |
| 2008/0305832 A1 | 12/2008 | Greenberg |
| 2009/0000969 A1 * | 1/2009 | Walker et al. ................ 206/307 |

(Continued)

FOREIGN PATENT DOCUMENTS

| WO | 2006102718 A1 | 10/2006 |
| WO | 2009021061 A1 | 2/2009 |

OTHER PUBLICATIONS

Kumar, Raakhee. "The FDA's Regulation of Mobile Technology as Medical Devices." Health Law Perspectives, Apr. 2010, Health Law & Policy Institute, University of Houston Law Center. <http://www.law.uh.edu/healthlaw/perspectives/2010/kumar-fdamobile.pdf>.

(Continued)

*Primary Examiner* — Nirav B Patel
*Assistant Examiner* — Mohammed Waliullah
(74) *Attorney, Agent, or Firm* — Maeve McCarthy; Jason Sosa (57) ABSTRACT

A tool for establishing a wireless connection from a mobile device to another device in proximity to the mobile device. The mobile device receives requests for data, such as a user profile, medical records, etc. from the device. The mobile device has the ability to register/preapprove the requesting device allowing the device to access the requested data. The mobile device also has the ability to give varying devices different authorization levels. The mobile device has the ability to store the data on another system, and in response to the request, validate the requesting device and the device's authorization level, request the data from the other system through a network, and return the data to the requesting device.

24 Claims, 8 Drawing Sheets

(56) References Cited

U.S. PATENT DOCUMENTS

| | | | |
|---|---|---|---|
| 2009/0017750 A1* | 1/2009 | Marcinkiewicz | 455/3.05 |
| 2009/0037224 A1 | 2/2009 | Raduchel | |
| 2009/0047923 A1 | 2/2009 | Jain et al. | |
| 2009/0158034 A1* | 6/2009 | Gu et al. | 713/156 |
| 2009/0271221 A1 | 10/2009 | Aridi et al. | |
| 2010/0015975 A1 | 1/2010 | Issa et al. | |
| 2010/0048159 A1 | 2/2010 | Stenquist | |
| 2010/0217694 A1* | 8/2010 | Knighton | 705/31 |
| 2011/0040578 A1 | 2/2011 | Ramsey | |
| 2011/0314515 A1* | 12/2011 | Hernoud et al. | 726/2 |
| 2012/0026971 A1* | 2/2012 | Khandelia et al. | 370/331 |

OTHER PUBLICATIONS

UTAGICE (in Case of Emergency). "UTAG—Digital Dogtag, ICE Card & UTAG Sports." Date printed Jun. 23, 2011 <http://www.utagice.com/acatalog/Credi.html>.

Alexandrou et al. "UBIMATE: A ubiquitous healthcare emergency platform." Manuscript received on Jun. 30, 2006.

Mapleridge, Ann. eHOW.com. "Bluetooth Technology Tutorials." Demand Media, Inc. Copyright 1999-2011. Date printed Jun. 23, 2011 <http://www.ehow.com/way_5271300_bluetooth-technology-tutorials.html>.

Howardforums. "Why can't I install Google's Car Home app—Page 3." Comment posted Feb. 25, 2011. Date printed Jun. 27, 2011 <http://www.howardforums.com/showthread.php/1701529-Why-can-t-I-install-Google-s-Car-Home-app/page3>.

Cleveland.com. "Online health information is going mobile, survey says." Published Oct. 19, 2010: updated Oct. 20, 2010 <http://www.cleveland.com/business/index.ssf/2010/10/online_health_information_is_g.html>.

Josef, Natalie. RepairPal Car Care Confidence. RepairPal Blog: Under the Hood. "Customizing your Vehicle Settings." Published Jan. 25, 2011 <http://repairpal.com/blog/customizing-your-vehicle-settings>.

Bravenet Blog. "The UGC Streaming Radio Group Web Journal." Published Mar. 18, 2007 <http://sparkle4u2nv.bravejournal.com/>.

Igbokwe, Obi. Biohealthmatics.com. "Wireless Technology and Healthcare." Copyright 2010. Page last updated Nov. 24, 2007 <http://www.biohealthmatics.com//Articles/0000000016.aspx>.

Wikipedia. "Bluetooth." Page last modified Jun. 22, 2011 <http://en.wikipedia.org/wiki/Bluetooth>.

Bluetooth.com "Medical and Health Devices." Bluetooth SIG, Inc., Copyright 2011. Date printed Apr. 7, 2011 <http://www.bluetooth.com/Pages/Medical.aspx>.

Iftode, Liviu et al., "Smart Phone: An Embedded System for Universal Interactions", Distributed Computing Systems, 2004. FTDCS 2004 Proceedings, 10th IEEE International Workshop on Future Trends of, May 26-28, 2004, pp. 88-94.

"Bluetooth", Wikipedia, http://en.wikipedia.org/wiki/Bluetooth, as of Aug. 8, 2013 (at 16:43), 23 pps.

"Near Field Communication", http://www.webopedia.com/TERM/N/Near_Field_Communication.html, as of Aug. 8, 2013, 2 pps.

"Near Field Communication", http://en.wikipedia.org/wiki/Near_field_communication, as of Aug. 8, 2013 at 13:08, 13 pps.

* cited by examiner

DATA MANAGEMENT WITH A NETWORKED MOBILE DEVICE

FIELD OF THE INVENTION

The present invention relates generally to data management and more specifically to managing medical and other types of data with a mobile device coupled to a network.

BACKGROUND OF THE INVENTION

Mobile computing devices that remain on or near a user have become prevalent in today's culture. An exemplary list of such mobile devices includes cellular phones, smart phones, personal digital assistants (PDAs), electronic watches, and even smart computer chips on credit cards. Mobile devices are often capable of storing a great deal of data and/or accessing data on a network via a wireless connection, such as a Wi-Fi connection or a cellular connection.

Additionally, multitudes of electronic devices surround us in many of our day to day activities, from computers, to vending machines, to ATMs, and even to the cars we drive. The computing capabilities of these electronic devices continue to progress at a rapid pace. Many of these electronic devices contain at least some base form of one or more processors, storage devices and memory, and even communication functionality.

It is known that electronic devices, including mobile computing devices, may scan for and communicate directly with one another. For example, RFID (radio-frequency identification) technology uses radio waves to transfer data between an RFID reading device and an RFID tag. The RFID tag comprises an integrated circuit for storing and processing data, modulating and demodulating RF signals, and performing other specialized functions. The RFID tag may also have an antenna that transmits the stored data to the RFID reading device.

Bluetooth™ technology is also known today to enable two-way, wireless communication for exchanging data over short distances. Bluetooth technology also makes use of radio transmissions and can communicate between fixed and mobile devices. Other wireless solutions are available to connect devices in close proximity.

Currently, a mobile device may connect to various devices as a user of the mobile device relocates to different areas. Once a connection is made, applications exist allowing the user of the mobile device to actively direct data to be sent to the connected electronic device. For example, US Patent Application 2009/0037224, herein incorporated by reference, describes that a user of a mobile device may initiate a request for medical records. The mobile device responsively sends requests to multiple different database providers that stored electronic medical records for the user. The multiple database providers send the requested medical records for the user to the mobile device. The mobile device may be configured to transfer the received medical records to an electronic device of a medical service provider.

SUMMARY

Aspects of the present invention disclose a method, computer system, and computer program product for managing data with a mobile device. The mobile device establishes a wireless connection with an electronic device while the mobile device is within a wireless range of the electronic device. With the wireless connection, the mobile device receives a request from the electronic device for one or more data files. In response, the mobile device wirelessly connects to a network device via a network different than the wireless connection to the electronic device. The mobile device sends authentication information for the mobile device to the network device. The mobile device requests the one or more data files from the network device. The mobile device receives the one or more data files from the network device, and finally, the mobile device sends the one or more data files to the electronic device.

BRIEF DESCRIPTION OF THE SEVERAL VIEWS OF THE DRAWINGS

FIGS. 3A and 3B are alternate embodiments illustrating the steps of two programs installed in the mobile computing device of FIG. 1 for acquiring approved connections for the mobile device to various electronic devices.

DETAILED DESCRIPTION

Figure 1:
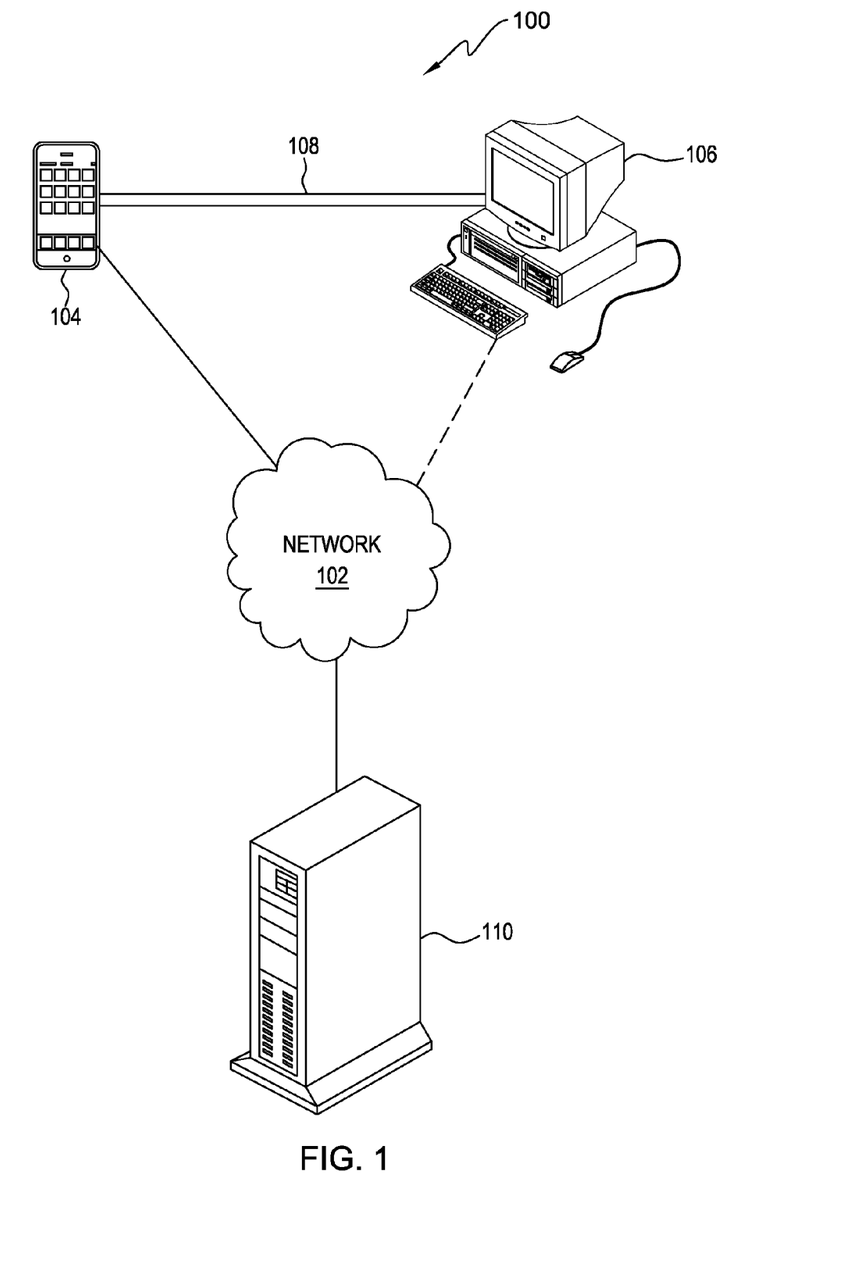
FIG. 1 depicts a distributed data processing system according to the present invention for managing medical and other types of data with a mobile computing device.

FIG. 1 illustrates a distributed data processing system generally designated 100 according to one embodiment of the present invention. FIG. 1 provides only an illustration of one implementation and does not imply any limitations with regard to the environments in which different embodiments may be implemented. Many modifications to the depicted environments may be made.

In the illustrated embodiment, data processing system 100 comprises a server computer 110 and a mobile computing device 104 (mobile device 104) interconnected by a network 102. Mobile device 104 is (long range) wirelessly connected to network 102 by Wi-Fi or cellular technology. Mobile device 104 also includes Bluetooth technology for short range wireless connection. In another embodiment, mobile device 104 may include RFID technology or another close proximity communications technique. Data processing system 100 also includes another computer 106 which includes Bluetooth technology for short range wireless connection to mobile device 104. As explained in more detail below, computer 106 requests and obtains data relating to an owner of mobile device 104. The data is stored on the mobile device 104 or alternatively on server computer 110, downloaded from server computer 110 by mobile device 104 pursuant to a request by computer 106, and passed-through mobile device 104 to computer 106.

Network 102 may include connections, such as wire, wireless communication links, or fiber optic cables. Server computer 110 may represent a "cloud" of computers interconnected by one or more networks.

When mobile device 104 finds itself in close proximity to a compatible device, such as computer 106, mobile device 104 can determine if proper permissions for communication exist (for example, by Bluetooth protocol and an Access Control List identifying computer 106) and if so, establish a connection. Mobile device 104 may be, for example, a handheld device or smart-phone, a personal digital assistant (PDA), an enhanced digital watch, a tablet computer, a notebook, a laptop computer, a thin client, or some other transitory computing device.

Computer 106 depicts one such compatible device capable of establishing a direct wireless connection 108 with mobile device 104. In the depicted embodiment, mobile device 104 is geographically near computer 106 (such as in the same room) and has established connection 108.

In a preferred embodiment, connection 108 facilitates a virtual private network (VPN) connection or another type of authenticated and/or encrypted connection sufficient to reasonably secure data exchanged over the connection. Bluetooth technology allows for such a connection.

A user of mobile device 104 can direct that mobile device 104 send data to computer 106 by establishing a connection to computer 106, fetching the data from server computer 110 and forwarding the data to computer 106 via a Bluetooth connection. There are other circumstances, however, where computer 106 controls receipt of the data (e.g., from server computer 110 via mobile device 104) with prior permission/authority from mobile device 104. For example, a request by computer 106 for preferences of the owner of mobile device 104 related to computer 106 might warrant an automatic flow of such preferences from the mobile device or from the server computer to the requesting device via the mobile device. As another example, a request for medical records from computer 106 for an owner of the mobile device as the owner enters a hospital (and comes into proximity with computer 106) may also warrant automated processing. Such automation requires management of data flowing into and out of the mobile device.

Though in one embodiment of the present invention, the data requested, or a portion of the data requested, may reside in the mobile device, in another embodiment, the requested data may reside, in whole or in part, on one or more separate computer systems. One such separate computer system is server computer 110 accessible to mobile device 104 through network 102. In the latter embodiment, mobile device 104 may still control or manage the flow of data while acting as a conduit between a requesting device, such as computer 106 and server computer 110.

Server computer 110 may be, for example, a server computer system such as a management server, a web server, or any other electronic device or computing system capable of receiving and sending data. Server computer 110 may be a primary server for a computing system utilizing clustered computers and components to act as a single pool of seamless resources when accessed through network 102. This is a common implementation for data centers and cloud computing applications.

In one embodiment computer 106 also connects to network 102 (as shown by the broken line in FIG. 1) via a wired or wireless connection. In another embodiment, computer 106 may be a stand-alone device removed from network 102. In another embodiment still, computer 106 may be removed from network 102, but connected to a separate local area network (LAN) (not shown).

Distributed data processing system 100 may include additional server computers, client computers, displays and other devices not shown.

Figure 8:
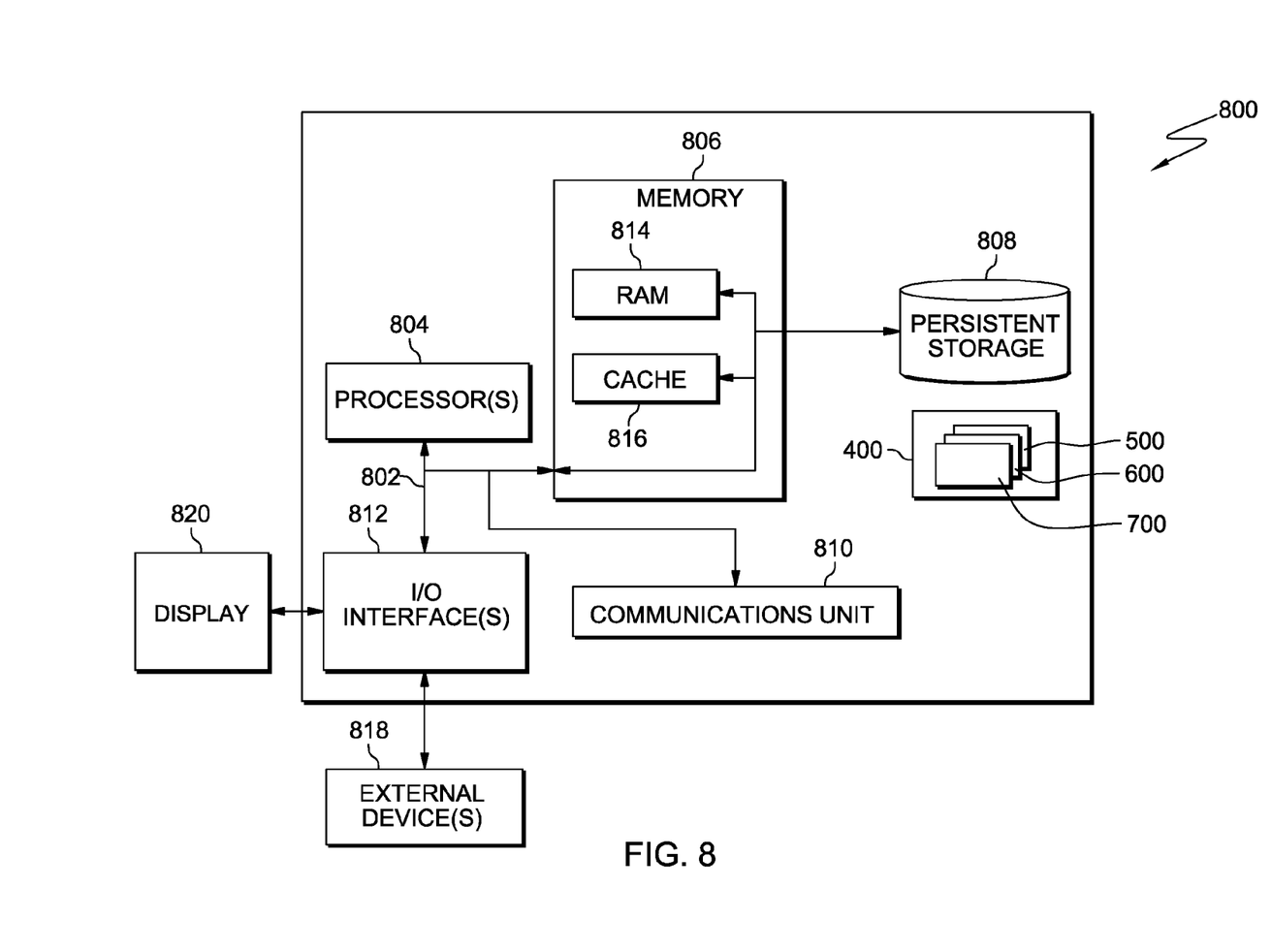
FIG. 8 is a block diagram of components of a data processing system (such as a mobile device, electronic device, or server computer) depicted in accordance with an illustrative embodiment.

Mobile device 104, computer 106, and server computer 110 each maintain respective system components. Exemplary components for these systems are illustrated in FIG. 8.

In the depicted example, network 102 is the Internet representing a worldwide collection of networks and gateways that use the Transmission Control Protocol/Internet Protocol suite of protocols to communicate with one another. Network 102 may also be implemented as a number of different types of networks, such as an intranet, a local area network (LAN), or a wide area network (WAN). FIG. 1 is intended as an example, and not as an architectural limitation for the different embodiments.

Figure 2:
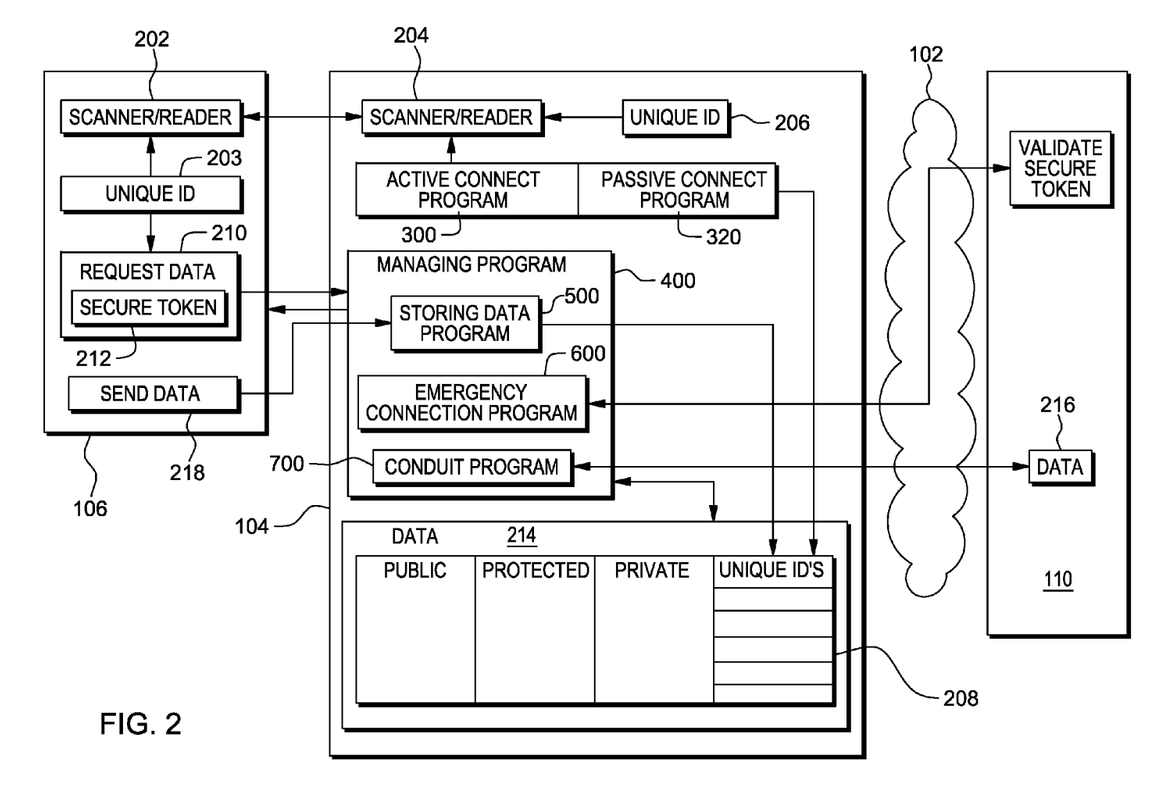
FIG. 2 depicts a data flow diagram between an electronic device, mobile device, and server computer of FIG. 1, in accordance with an embodiment of the invention.

FIG. 2 depicts a data flow diagram between computer 106, mobile device 104, and server computer 110, in accordance with an embodiment of the invention.

Respective scanner/reader devices 202 and 204 operate on computer 106 and mobile device 104. Scanner/reader device 202 automatically passes along computer 106's unique ID 203. Active connect program 300 or passive connect program 320 control whether mobile device 104 returns its own unique ID 206 and allocates storage space 208 for approved connections.

If the connection is approved, request data program 210 can request information from managing program 400. If unique ID 203 has not been approved, request data program 210 may send secure token 212 to managing program 400. Managing program 400 will in turn execute emergency connection program 600 to connect to server computer 110, via network 102, to validate secure token 212. If managing program 400 determines that computer 106 is authorized to access the requested data, managing program 400 locates the requested data in data storage 214 and returns the data to computer 106. As an alternative, managing program 400 may direct conduit program 700 to locate the data in data storage 216 on server computer 110 via network 102. In another embodiment, the functionality to validate a secure token and data storage 216 may be on separate computer systems.

Computer 106 may also send data to be stored in its own storage space 208. Send data functionality 218 sends the data and storing data program 500 of managing program 400 determines if the data may be stored. Storing data program 500 may place the data in storage space 208. In an alternate embodiment storing data program 500 may use conduit program 700 to store the data in data storage 216.

Figure 3A:
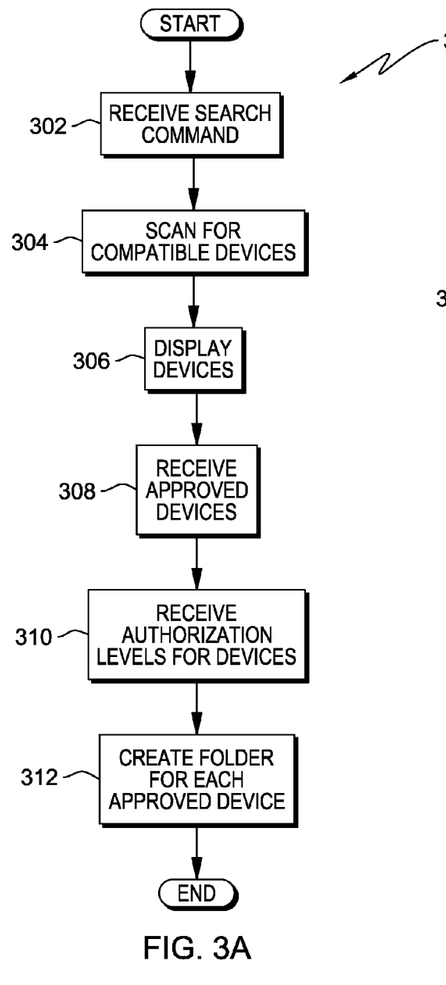
FIG. 3A is a flowchart of the steps of an active connect program residing on the mobile device of FIG. 1, and representing an embodiment that actively seeks out computing devices in the area and determines if connection to each of the devices is approved.
Figure 3B:
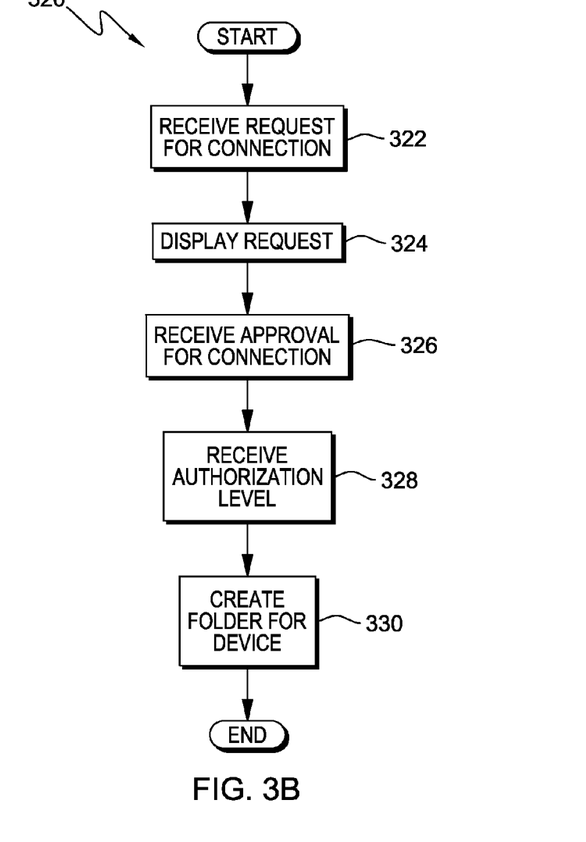
FIG. 3B is a flowchart of the steps of a passive connect program residing on the mobile device of FIG. 1 and waiting for a compatible computing device to seek out the mobile device in accordance to an embodiment of the present invention.

FIGS. 3A and 3B are flowcharts of alternative embodiments of a connection program, herein referred to as active connect program 300 and passive connect program 320 for acquiring approved connections for a mobile device to various electronic devices. Using Bluetooth to establish a connection, in order for two devices to connect to each other, they must be "paired." To accomplish this, each device must know a unique ID specific to the other. This is the preferred embodiment as such a connection maintains a higher degree of security and prohibits unwanted devices from connecting to a user's mobile device. Generally, a device's unique ID may be broadcast from the device to another compatible device. This may occur automatically or at the direction of a user of the device. Alternatively, another device's unique ID may be manually entered into a device by a user.

Active connect program 300 resides on mobile device 104 and represents one embodiment for a program that actively seeks out devices in the area and determines if connection to each of the devices is approved.

First, active connect program 300 receives an indication (via a keyboard or GUI) from a user of mobile device 104 to search for compatible devices (step 302). Following such an indication, active connect program 300 scans the area for compatible devices (step 304), for example, by scanning radio frequencies.

Active connect program 300 displays any devices discovered to the user (step 306). Active connect program 300 receives a selection of one or more devices, such as computer 106, that the user approves for connection (step 308). For example, the display might list compatible devices with a check box next to each listing. The user could select or "check" the desired boxes and submit the selections as approved.

In one implementation, it is envisioned that compatible devices communicate a unique ID to the mobile device automatically. Upon approval of a connection, mobile device 104 communicates its own unique ID to the compatible device so that that mobile device 104 and the compatible device can pair. Once two devices are paired, they may automatically connect when in range of each other. In another embodiment, mobile device 104 may also communicate a pass phrase to the compatible device upon approval. For the compatible device to automatically reconnect at later time, it may have to send the pass phrase in addition to its unique ID.

In a preferred embodiment, active connect program 300 also receives a selection, from the user, of an authorization level for each of the compatible devices approved (step 310). The authorization level may be saved with the unique ID of the device to later determine what data an approved device has access to. For example, an approved hospital computer might have the highest authorization level so that it might request sensitive medical documents.

Also in a preferred embodiment, active connect program 300 creates a folder for each approved device (step 312). The folder is associated with the approved device's unique ID. In addition to having access to different levels of data depending on authorization, such a folder may be dedicated and accessible only to the device it corresponds to. This would allow a device to put a small amount of data on the user's mobile device and request that information at a later date. Personalization of services may be provided in this manner.

Passive connect program 320, on the other hand, also resides on mobile device 104, but waits for a compatible device to seek out mobile device 104 and attempt a connection.

Passive connect program 320 begins by receiving a request for a connection from a compatible device (step 322), such as computer 106. Passive connect program 320 displays the request to the user of mobile device 104 (step 324). In response, passive connect program 320 receives approval for the connection from the user (step 326).

Again, along with approval, in one embodiment mobile device 104 sends its own unique ID for pairing to the requesting device.

Passive connect program 320 also receives an authorization level for the approved device in the preferred embodiment (step 328). Finally, passive connect program 320 creates a folder for the device (step 330) associated with the device's unique ID.

Figure 4:
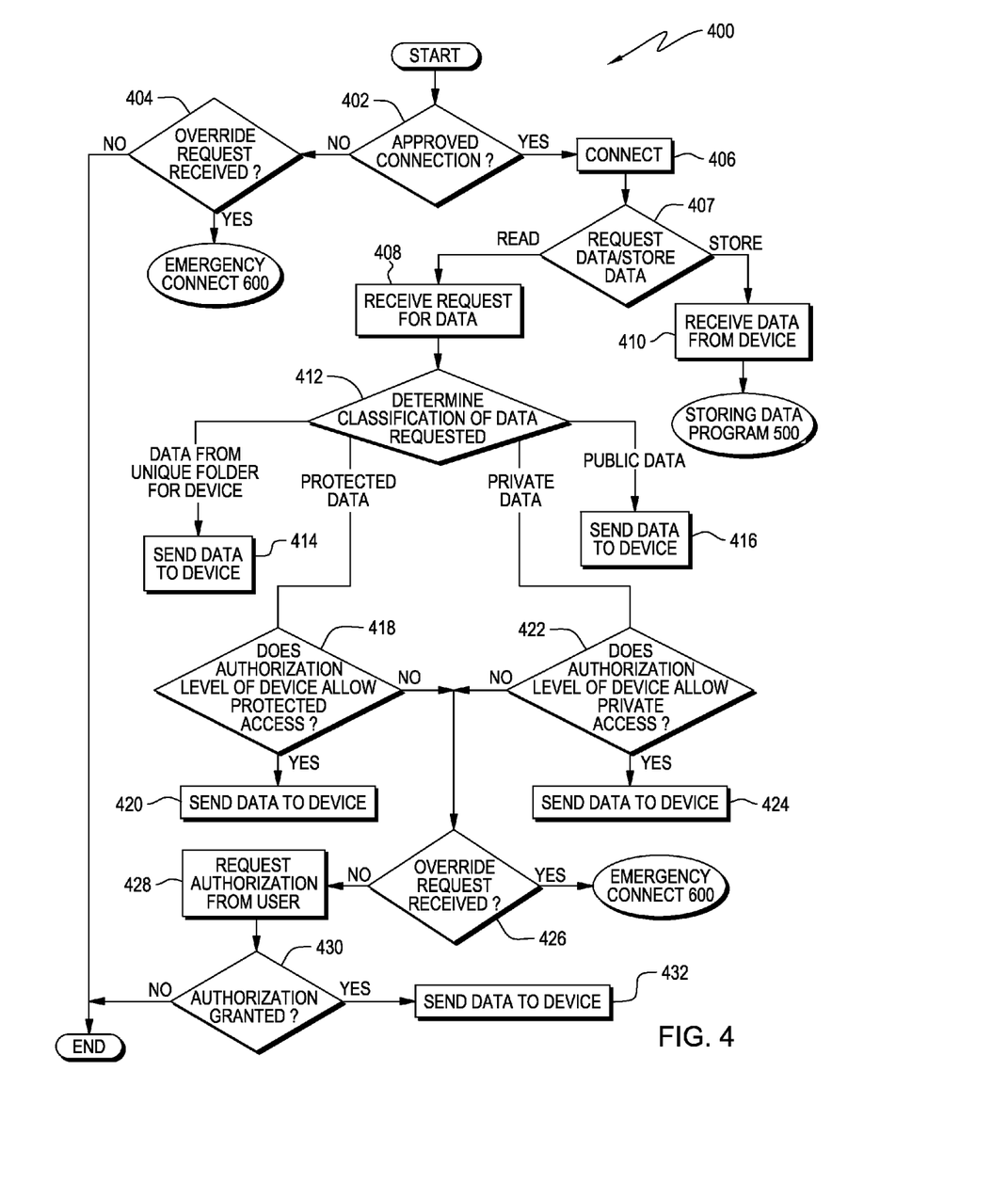
FIG. 4 is a flowchart of the steps of a managing program installed on the mobile device of FIG. 1 that manages the data flow between the mobile device of FIG. 1 and a compatible electronic computing device in accordance with an embodiment of the present invention.

FIG. 4 depicts the steps of a flowchart for managing program 400 that manages the data flow between mobile device 104 and computer 106.

First, managing program 400 determines if the there is an approved connection between mobile device 104 and computer 106 (decision block 402). This can be accomplished, for example, by locating the saved approval for computer 106's unique ID. If there is not an approved connection, managing program 400 determines if an override request has been received (decision block 404), and if not, managing program 400 ends. An override request to connect to mobile device 104 without prior user approval may be necessary in limited emergency cases such as where a patient is unconscious and a hospital computer is requesting medical records. If managing program 400 receives an override request, managing program 400 runs emergency connection program 600 (depicted in FIG. 6) to determine if a forced connection is warranted and to grant access to data.

If the connection is approved, managing program 400 connects to computer 106 (step 406). Once the connection is established, managing program 400 waits for input from computer 106 and determines if the input is a request for data or if the input is data to be stored (decision 407). In response, managing program 400 will either receive the request for data (step 408) or receive the data for storage from computer 106 (step 410). If managing program 400 receives data from computer 106 (step 410), managing program 400 runs storing data program 500 (depicted in FIG. 5) to determine if mobile device 104 will accept the data.

If instead managing program 400 receives a request for data, managing program 400 determines the classification for the data requested (decision block 412). For example, mobile device 104 may maintain, or have access to, standard folders accessible to devices connecting to the mobile device and having proper authorization. One example would be a division between public files (accessible to any device that connects to the mobile device), protected (accessible to a restricted class of devices), and private (accessible to a very limited number of devices—or potentially, never accessible). Additionally, data may be classified as belonging to a specific device (i.e., data stored in the unique folder created for the device). For the purposes of discussion and teaching, the aforementioned exemplary classes are used in the depicted flowchart.

If in response to the determination of class, managing program 400 determines that the requested data is from the data stored in computer 106's unique folder, managing program 400 sends the data to the computer 106 (step 414).

If in response to the determination of class, managing program 400 determines that the requested data is public data, managing program 400 sends the data to the computer 106 (step 416).

If in response to the determination of class, managing program 400 determines that the requested data is protected data, managing program 400 determines if the authorization level of computer 106 allows computer 106 to access protected data (decision block 418). The user preferably has the ability to associate a unique device ID with an authorization level, for example, when approving the connection. If the authorization level is sufficient, managing program 400 sends the requested data to computer 106 (step 420).

Similarly, if the requested data is private, managing program 400 determines if the authorization level of computer 106 allows computer 106 to access private data (decision block 422) and if the authorization level is sufficient, sends the data to computer 106 (step 424).

Figure 6:
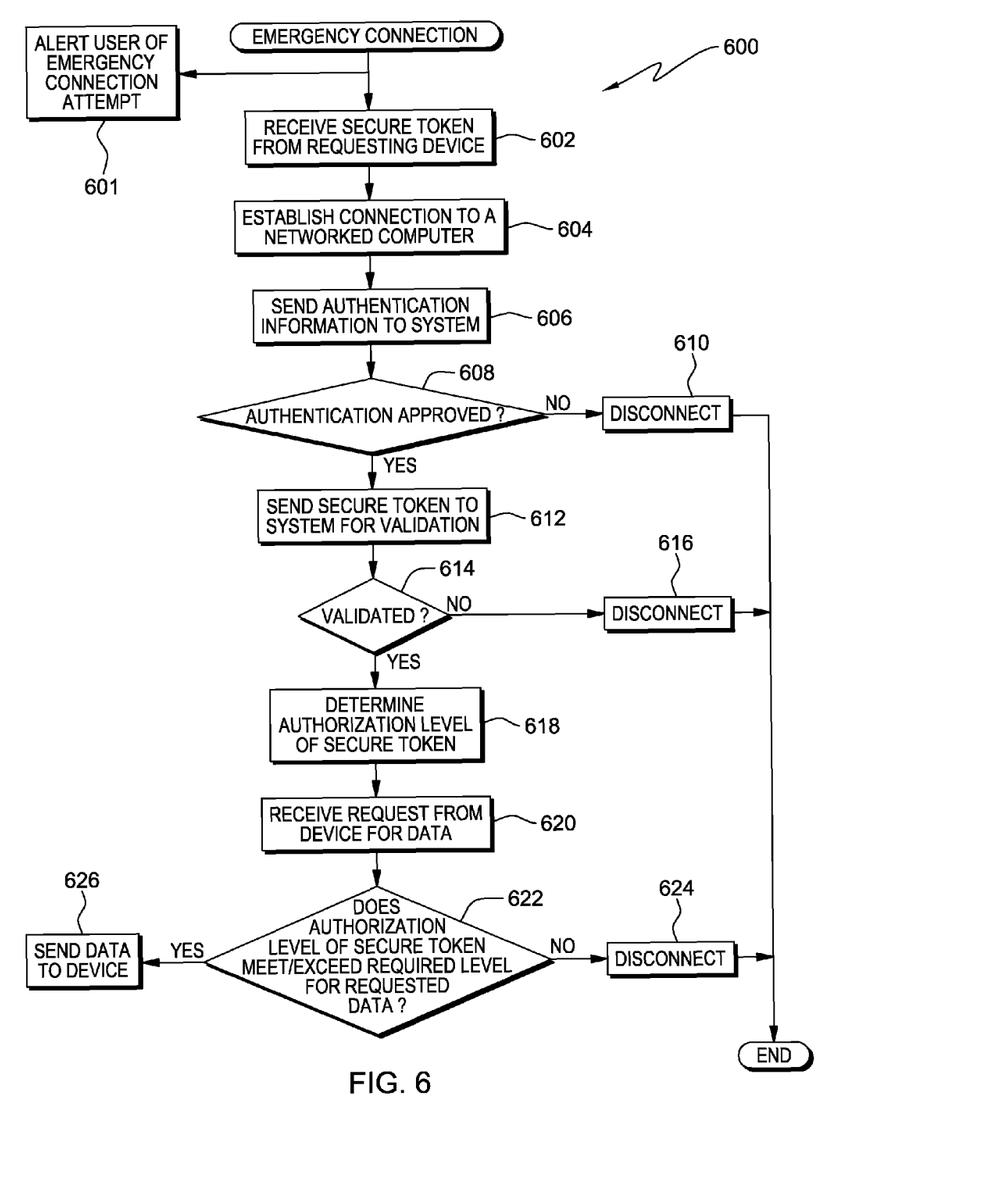
FIG. 6 is a flowchart of the steps of an emergency connection program installed on the mobile device of FIG. 1 for determining if connection and authorization to access data should be granted without express permission from the user of the mobile device, in accordance with an embodiment of the invention.

However, if either decision block 418 or decision block 422 determines that the authorization level is insufficient, managing program 400 determines if there has been an override request received (decision block 426). If there has been an override request, managing program runs emergency connection program 600. Otherwise, managing program 400 displays the request to the user and requests authorization from the user (step 428).

Managing program 400 determines if the user grants authorization (decision block 430). In a preferred embodiment, the user is given a choice to select: "allow once," "allow always," or "deny request." If "allow always" is selected, managing program 400 increases the authorization level associated with computer 106.

In either case, if authorization is granted, managing program 400 sends the requested data to computer 106 (step 432).

Figure 5:
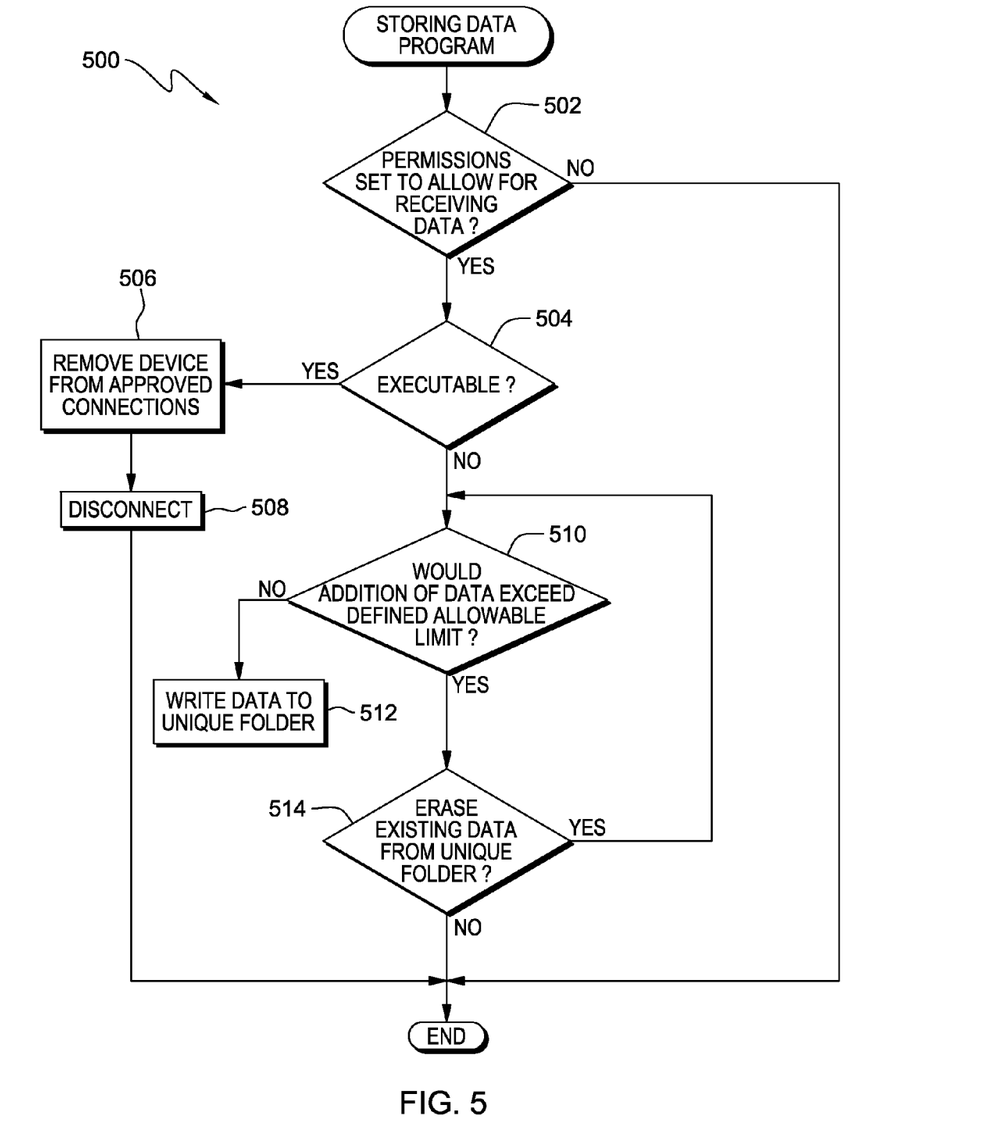
FIG. 5 is a flowchart of the steps of a storing data program installed on the mobile device of FIG. 1 for determining if data received at the mobile device of FIG. 1 will be stored, in accordance with an embodiment of the present invention.

FIG. 5 illustrates the steps of a flowchart for storing data program 500 in accordance with an embodiment of the present invention. Storing data program 500 determines whether mobile device 104 will accept and store data sent to mobile device 104 from computer 106.

Upon receiving data for storage, storing data program 500 first determines if permissions are set on mobile device 104 to allow for computer 106 to write to mobile device 104 (decision block 502). If the permissions do not allow this action, storing data program 500 ends. Otherwise, storing data program 500, preferably, examines the data to be stored.

In the depicted embodiment, storage data program 500 determines if the data is an executable file (decision block 504). Executables may be indicative of a virus and in response to detecting one, storing data program 500 removes computer 106 from the list of approved connections (step 506), disconnects from computer 106 (step 508), and ends.

If the data is not an executable file, storing data program 500 determines if storing the data would exceed a defined allowable limit of storage for computer 106 (decision block 510). If the allowable limit would not be exceeded, storing data program 500 writes the data to the unique folder created for computer 106 (step 512). In the preferred embodiment, this reserved storage space is the only space that may be written to.

If the amount of data would exceed the allowable limit, storing data program 500 determines if existing data in the unique folder should be erased (decision block 514). This may be done in a variety of ways. In one embodiment, storing data program 500 will erase the existing data if it determines that doing so will create enough room for the new data. In another embodiment, storing data program 500 will prompt computer 106 for a determination if all or part of the existing files should be removed. If it is determined that no files or data should be removed, storing data program 500 ends. In the case that existing data is removed, storing data program 500 returns to decision block 510 to determine if adding the new data would still exceed the allowable limit.

FIG. 6 depicts the steps of a flowchart for emergency connection program 600 for determining if connection and authorization to access data should be granted without express permission from the user of mobile device 104, in accordance with an embodiment of the invention. The preferred authentication and authorization technique is a multi-factor authentication process using secure tokens. As used herein, a token is a unique software object given to a specific user to prove the user's identity.

In response to receiving some indication of a special circumstance, such as an override request as discussed in FIG. 4, emergency connection program 600 attempts to notify the user of mobile device 104 of the emergency connection attempt (step 601). This step does not prevent the attempt, but ensures that whether the connection is successful or unsuccessful, that the user is at some point made aware that the access was attempted. The notification may involve sending a note to one or more of the user's email addresses, sending the mobile device a text message, etc. Other embodiments may send notifications only on successful connections or only on unsuccessful attempts. Another embodiment may be devoid of this step entirely. Independent of step 601, emergency connection program 600 receives a secure token from computer 106 requesting the connection (step 602).

Instead of authenticating the token locally, for security purposes, emergency connection program 600 on mobile device 104 establishes a connection to a networked computing system, such as server computer 110 (step 604). Mobile device 104 preferably has the ability to wirelessly connect to network 102. Server computer 110 is preferably a dedicated authentication server.

Emergency connection program 600 sends authentication information for mobile device 104 to server computer 110 (step 606). The authentication information is preferably a separate token enabling server computer 110 to identify and authenticate the mobile device. Access to server computer 110 is denied unless mobile device 104 is an approved device.

Emergency connection program 600 determines if mobile device 104 authentication was approved (decision block 608). If authentication of mobile device 104 is not approved, emergency connection program 600 disconnects from the computer 106 (step 610).

If mobile device 104 is authenticated, emergency connection program 600 forwards the secure token received from the computer 106 to the server computer 110 for validation (step 612). Server computer 110 preferably updates registered classes of devices with new security tokens. For example, hospitals may register their computers with such a service. Server computer 110 may send the registered computers a secure token and update the token from time to time. When an emergency occurs and a user is brought into a hospital, even if the user has not specifically registered or paired the user's mobile device with devices in the hospital, if the mobile device has registered with the networked computer system (i.e., server computer 110), the hospital computer can send the secure token to the mobile device, which can in turn forward the token to the networked computing system for validation. Preferably, only the networked computing system contains the proper decryption keys to validate the token.

Emergency connection program 600 determines if the token has been validated (decision block 614), and in response to the token not being validated, disconnects from computer 106 (step 616). If the token is validated, emergency connection program 600 determines the authorization level of the secure token (step 618). For example, server computer 110 may give a different token to a hospital computer than it does to a firehouse computer. Both tokens may be valid, but the hospital computer may have greater access to medical records. Another embodiment may be devoid of this step.

Emergency connection program 600 receives a request from computer 106 for data (step 620). In one embodiment this occurs after the secure token has been authenticated. In other embodiments this may occur prior to or concurrent with the receiving of the secure token.

Emergency connection program 600 determines if the authorization level associated with the secure token matches the level required to access the data (decision block 622). If the authorization level is not high enough, emergency connection program 600 disconnects from computer 106 (step 624). If the authorization level is high enough, emergency connection program 600 sends the requested data to computer 106 (step 626).

Figure 7:
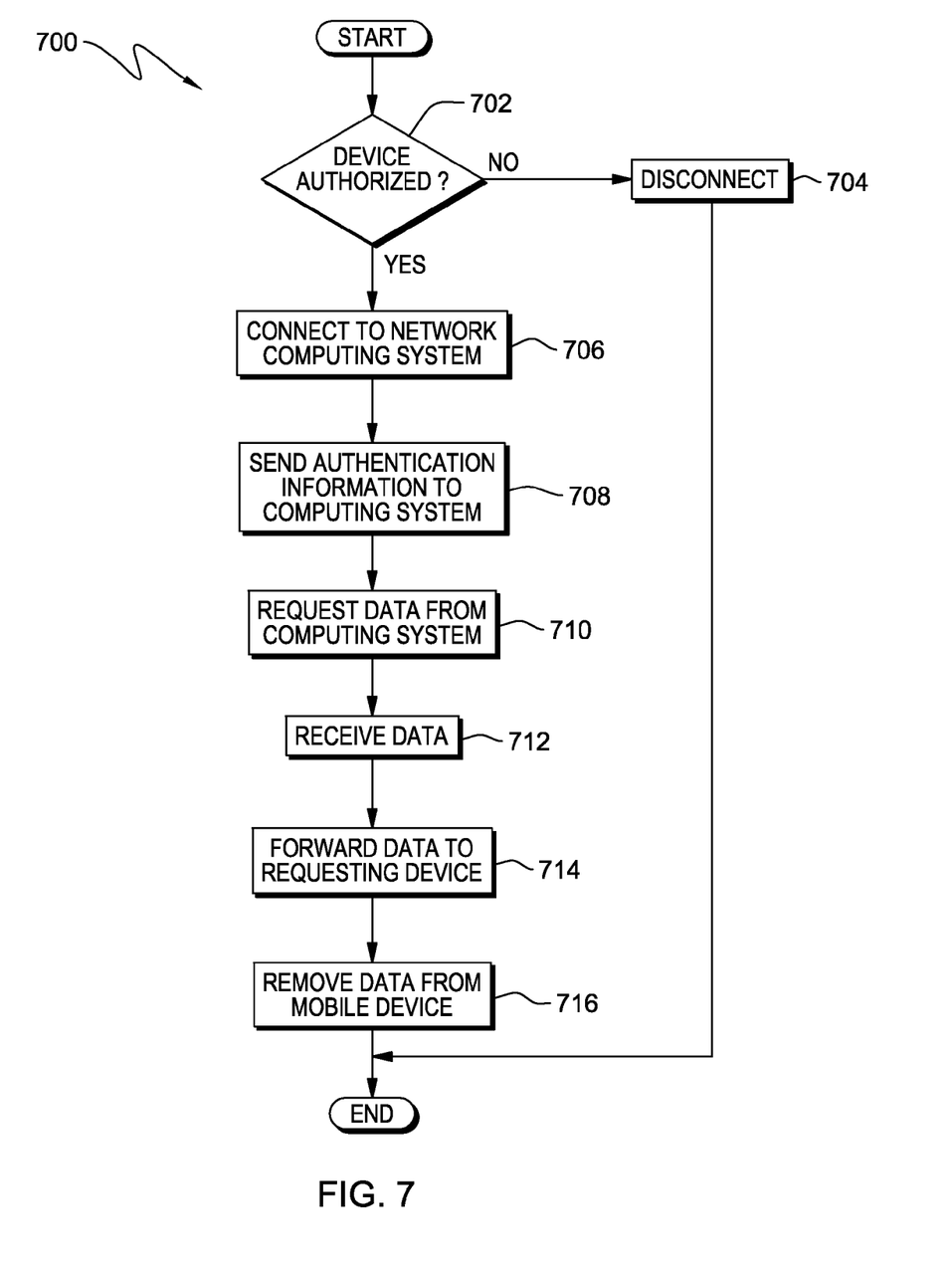
FIG. 7 illustrates the steps of a program installed on the mobile device of FIG. 1 for managing the access and transfer of data from a mobile device when the data is not stored locally on the mobile device, i.e., a conduit program, in accordance with an embodiment of the invention.

FIG. 7 illustrates the steps of conduit program 700 for managing the access and transfer of data from a mobile device when the data is not stored locally on the mobile device, in accordance with an embodiment of the invention.

As discussed earlier, the data requested by a compatible device connecting to a mobile device need not be stored locally on the mobile device. In some instances it may be preferred that the data is not stored locally. For example, certain data, such as medical records, may be very sensitive. Storing such records on a mobile device may be a security risk and subject the data to those trying to obtain it improperly. Furthermore, if a multitude of electronic devices are made to be compatible with the above discussed embodiments of the present invention, it may become unfeasible to allot each device space in local storage. Storing data on another computer system accessible through a network has the ability to provide flexibility, scalability, and security. Exemplary computer systems include a home computer, a server computer, a data center system, and a cloud computing environment.

The functionality of conduit program 700 may be included in any of the above process flows prior to sending the requested data to the requesting device.

Conduit program 700 begins by confirming that the requesting device (computer 106) is authorized to access the requested data (decision block 702). If computer 106 is not authorized, conduit program 700 disconnects from computer 106 (step 704). Otherwise, conduit program 700 establishes a connection with a network computing system, such as server computer 110, containing the data (step 706). In another embodiment, the network computing system containing the data is a separate computing system than that used to authenticate secure tokens from a compatible device requesting data.

Conduit program 700 sends authentication information for mobile device 104 to the server computer 110 (step 708). Similar to emergency connection program 700, it is desirable that only a mobile device registered with the server computer 110 has access to the data associated with that mobile device.

Subsequent to sending the proper authorization information, conduit program 700 requests the data from server computer 110 (step 710). In another embodiment, the authentication information and the request for data may be sent in reverse order or substantially at the same time.

Conduit program 700 receives the data (step 712) and forwards the data to computer 106 (step 714). After the data is forwarded to computer 106, conduit program 700 preferably removes the data from mobile device 104 (step 716). If it is beneficial to store the data separately, it is likely beneficial to remove the local copy. In one embodiment, a user of mobile device 104 cannot see the data that is transferred without some other user interaction, such as a password. In this manner, even if mobile device 104 is stolen, only an authorized connecting device might access sensitive information, and not an improper user of the mobile device.

The following are examples of functionality offered by the present invention.

The user has mobile device 104 which is Bluetooth capable. To set up the process, the user, via mobile device 104, registers with a network computer, such as server computer 110, and supplies to server computer 110 the user's medical history as a user profile. This is supplied via a secure connection. With this registration, mobile device 104 can later download the user's profile upon request. The registration may later be authenticated through the use of a secure token, password, cookies, etc. The user, via mobile device 104, also registers with a medical service which will authorize hospital computers and other medical service computers, such as computer 106, to request the user's profile from mobile device 104 (with a security code/authentication) if the user is unconscious.

In one scenario, the user with mobile device 104 arrives conscious at a hospital, and logs on to mobile device 104 and requests to supply the user's profile to a preapproved hospital computer, such as computer 106. In response, the user's mobile device makes a secure Bluetooth connection with a hospital computer. Next, the user's mobile device requests the user's profile from the server computer 110 via network 102, and upon receipt, forwards the user's profile to the hospital computer via the Bluetooth connection. There can be additional security between the mobile device 104 and the hospital computer to safeguard the user's profile. Next, the hospital computer processes the user's profile, for example, alerting a physician of pre-existing medical conditions.

In another scenario, the user with mobile device 104 arrives unconscious at a hospital. A hospital employee selects an option to request from the user's mobile device 104 the user's profile. Because the user had previously registered with the hospital service to authorize the hospital to obtain the user's profile if the user is unconscious, the hospital computer makes a secure Bluetooth connection with mobile device 104 and requests the user's profile. In response, mobile device 104 automatically requests the user's profile from server computer 110 and provides the user ID and password for the owner of the mobile device, and upon receipt of the user's profile, forwards the user's profile to the hospital computer via the Bluetooth connection. There can be additional security between mobile device 104 and the hospital computer to safeguard the user's profile. Next, the hospital computer processes the user's profile, for example, alerting a physician of pre-existing medical conditions.

In a third scenario, the user with mobile device 104 arrives unconscious at a hospital, but the user has not registered mobile device 104 with the hospital computer. However, if the hospital computer is registered with a medical service provider approved by the user, the hospital computer may have received a secure token from the medical service provider. The hospital computer sends the secure token to mobile device 104. Mobile device 104 sends the secure token to server computer 110, where server computer 110 belongs to or is registered with the medical service provider. Server computer 110 validates the secure token. In response, mobile device 104 approves the connection with the hospital computer. The hospital computer can then request the user profile from mobile device 104. In response, mobile device 104 automatically requests the user's profile from server computer 110, and upon receipt, forwards the user's profile to the hospital computer via the Bluetooth connection.

FIG. 8 depicts a block diagram of components of a data processing system (such as mobile device 104, computer 106, or server computer 110) depicted in accordance with an illustrative embodiment. It should be appreciated that FIG. 8 provides only an illustration of one implementation and does not imply any limitations with regard to the environments in which different embodiments may be implemented. Many modifications to the depicted environments may be made.

Data processing system 800 is representative of any electronic device capable of executing machine-readable program instructions. Data processing system 800 may be representative of a smart phone, an electronic digital watch, a computer system, PDA, or other electronic device.

Examples of well-known computing systems, environments, and/or configurations that may be suitable for use with data processing system 800 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Data processing system 800 includes communications fabric 802, which provides communications between processor(s) 804, memory 806, persistent storage 808, communications unit 810, and input/output (I/O) interface(s) 812.

Memory 806 and persistent storage 808 are examples of computer-readable tangible storage devices. A storage device is any piece of hardware that is capable of storing information, such as data, program code in functional form, and/or other suitable information on a temporary basis and/or permanent basis. The term "storage device" does not encompass signal propagation media, such as a copper cable, optical fiber or wireless transmission media. Memory 806 may be, for example, one or more random access memories (RAM) 814, cache memory 816, or any other suitable volatile or non-volatile storage device.

Managing program 400 with functionalities storing data program 500, emergency connection program 600, and conduit program 700 are stored in persistent storage 808 for execution by one or more of the respective processors 804 via one or more storage devices of memory 806. In the embodiment illustrated in FIG. 8, persistent storage 808 includes flash memory. Alternatively, or in addition to, persistent storage 808 may include a magnetic disk storage device of an internal hard drive, a solid state drive, a semiconductor storage device, read-only memory (ROM), EPROM, or any other computer-readable tangible storage device that is capable of storing program instructions or digital information.

The media used by persistent storage 808 may also be removable. For example, a removable hard drive may be used for persistent storage 808. Other examples include an optical or magnetic disk that is inserted into a drive for transfer onto another storage device that is also a part of persistent storage 808, or other removable storage devices such as a thumb drive or smart card.

Communications unit 810, in these examples, provides for communications with other data processing systems or devices. In these examples, communications unit 810 may include a radio transmitter and a radio receiver. In another embodiment, communications unit 810 is a network interface card. Communications unit 810 may provide communications through the use of either or both physical and wireless communications links. In another embodiment still, data processing system 800 may be devoid of communications unit 810. Managing program 400, storing data program 500, emergency connection program 600, and conduit program 700 may be downloaded to persistent storage 808 through communications unit 810.

I/O interface(s) 812 allows for input and output of data with other devices that may be connected to data processing system 800. For example, I/O interface 812 may provide a connection to external devices 818 such as a keyboard, keypad, a touch screen, and/or some other suitable input device. I/O interface(s) may also connect to a display 820.

Display 820 provides a mechanism to display information to a user. In a preferred embodiment, display 820 is the screen of a cell phone.

The aforementioned programs can be written in various programming languages (such as Java or C++) including low-level, high-level, object-oriented or non object-oriented languages. Alternatively, the functions of the aforementioned programs can be implemented in whole or in part by computer circuits and other hardware (not shown).

Based on the foregoing, a method, computer system, and computer program product have been disclosed for managing data with a mobile device. However, numerous modifications and substitutions can be made without deviating from the scope of the present invention. In this regard, each block in the flowcharts or block diagrams may represent a module, segment, or portion of code, which comprises one or more executable instructions for implementing the specified logical functions(s). It should also be noted that, in some alternative implementations, the functions noted in the block may occur out of the order noted in the figures. Therefore, the present invention has been disclosed by way of example and not limitation.

What is claimed is:

1. A method for managing data with a mobile device, the method comprising the steps of:
the mobile device establishing a wireless Near-Field Communication (NFC) connection with an electronic device;
the mobile device receiving, from the electronic device, an indication of an emergency involving a user of the mobile device who will not be asked to help obtain a data file needed to handle the emergency, the indication including a secure token unique to the electronic device and a request for the electronic device to connect to the mobile device without approval from the user;
the mobile device, without involvement of the user, automatically wirelessly connecting, via a network, to a server which has access to the data file, and automatically sending, to the server, authentication information identifying the mobile device;
the mobile device receiving, from the server, approval of the authentication information, and, in response, the mobile device automatically sending the secure token to the server for validation;
the mobile device receiving, from the server, validation of the secure token, and in response, the mobile device connecting to the electronic device;
the mobile device receiving a request, via the wireless NFC connection, from the electronic device for the data file;
the mobile device sending the request for the data file to the server;
the mobile device receiving the data file from the server; and
the mobile device sending the data file to the electronic device.

2. The method of claim 1, further comprising the prior step of the mobile device scanning a surrounding area for compatible electronic devices, and in response, locating the electronic device.

3. The method of claim 1, wherein the authentication information is selected from a list consisting of: a secure token, a passphrase, cookies, an encrypted key, a unique ID, a userID and password, and combinations thereof.

4. The method of claim 1, further comprising the steps of:
the mobile device determining an authorization level of the secure token in response to receiving validation of the secure token;
the mobile device determining a required authorization level of the requested data file; and
the mobile device determining the authorization level of the secure token meets or exceeds the required authorization level of the requested data file, and in response to the determination, the mobile device sending the requested data file to the electronic device.

5. The method of claim 4, wherein the mobile device determines the authorization level of the secure token does not meet or exceed the required authorization level of the requested data file, and the mobile device disconnects from the electronic device.

6. The method of claim 1, wherein the step of receiving the secure token from the electronic device is responsive to the mobile device determining that the electronic device is not currently authorized to access the data file.

7. The method of claim 1 further comprising the step of sending a message to a known user of the mobile device notifying the known user of the mobile device that the data file was requested.

8. The method of claim 1, wherein, subsequent to receiving the data file on the mobile device, the mobile device determining whether the data file can be stored on the mobile device; and
responsive to determining the data file can be stored on the mobile device, the mobile device storing the data file.

9. A computer system comprising one or more processors, one or more computer-readable memories, one or more computer-readable, tangible storage devices and program instructions which are stored on the one or more storage devices for execution by the one or more processors via the one or more memories and when executed by the one or more processors perform the method of claim 1.

10. The method of claim 1,
wherein the electronic device requesting the data file is operated by a medical service provider;
wherein the requested data file is a medical record of a registered user of the mobile device; and
wherein validation of the secure token unique to the electronic device verifies that the electronic device is operated by the medical service provider.

11. A computer program product for managing data with a mobile device, the computer program product comprising:
one or more computer-readable storage devices and program instructions stored on the one or more storage devices, the program instructions comprising:
program instructions to establish a wireless Near-Field Communication (NFC) connection with an electronic device;
program instructions to receive, from the electronic device, an indication of an emergency involving a user of the mobile device who will not be asked to help obtain a data file needed to handle the emergency, the indication including a secure token unique to the electronic device and a request for the electronic device to connect to the mobile device without approval from the user;
program instructions to, without involvement of the user, automatically wirelessly connect, via a network, to a server which has access to the data file, and automatically send, to the server authentication information identifying the mobile device;
program instructions to receive, from the server, approval of the authentication information, and, in response, the mobile device automatically sending the secure token to the server for validation;
program instructions to receive, from the server, validation of the secure token, and in response, program instructions to connect to the electronic device;
program instructions to receive a request, via the wireless NFC connection, from the electronic device for the data file;
program instructions to send the request for the data file to the server;
program instructions to receive the data file from the server; and
program instructions to send the data file to the electronic device.

12. The computer program product of claim 11, further comprising program instructions, stored on the one or more storage devices, to scan a surrounding area for compatible electronic devices, and in response, locate the electronic device.

13. The computer program product of claim 11, wherein the authentication information is selected from a list consisting of: a secure token, a passphrase, cookies, an encrypted key, a unique ID, a userID and password, and combinations thereof.

14. The computer program product of claim 11, further comprising program instructions, stored on the one or more storage devices, to:
determine an authorization level of the secure token in response to receiving validation of the secure token;
determine a required authorization level of the requested data files; and
determine the authorization level of the secure token meets or exceeds the required authorization level of the requested data file, and in response to the determination, send the requested data file to the electronic device.

15. The computer program product of claim 11, wherein the program instructions to receive the secure token from the electronic device are executed responsive to determining that the electronic device is not currently authorized to access the data file.

16. The computer program product of claim 11, further comprising program instructions, stored on the one or more storage devices, to send a message to a known user of the mobile device notifying the known user of the mobile device that the data file was requested.

17. The computer program product of claim 11, further comprising, subsequent to receiving the data file on the mobile device, program instructions, stored on the one or more storage devices, to determine whether the data file can be stored on the mobile device; and
responsive to determining the data file can be stored on the mobile device, program instructions to store the data file.

18. A computer system for managing data with a mobile device, the computer system comprising:
one or more processors, one or more computer-readable memories, one or more computer-readable, storage devices and program instructions which are stored on the one or more storage devices for execution by the one or more processors via the one or more memories, the program instructions comprising:

program instructions to establish a wireless Near-Field Communication (NFC) connection with an electronic device;

program instructions to receive, from the electronic device, an indication of an emergency involving a user of the mobile device who will not be asked to help obtain a data file needed to handle the emergency, the indication including a secure token unique to the electronic device and a request for the electronic device to connect to the mobile device without approval from the user;

program instructions to, without involvement of the user, automatically wirelessly connect, via a network, to a server which has access to the data file, and automatically send, to the server, authentication information identifying the mobile device;

program instructions to receive, from the server, approval of the authentication information, and, in response, the mobile device automatically sending the secure token to the server for validation;

program instructions to receive, from the server, validation of the secure token, and in response, program instructions to connect to the electronic device;

program instructions to receive a request, via the wireless NFC connection, from the electronic device for the data file;

program instructions to send the request for the data file to the server;

program instructions to receive the data file from the server; and program instructions to send the data file to the electronic device.

19. The computer system of claim 18, further comprising program instructions, stored on the one or more storage devices for execution by the one or more processors via the one or more memories, to scan a surrounding area for compatible electronic devices, and in response, locate the electronic device.

20. The computer system of claim 18, wherein the authentication information is selected from a list consisting of: a secure token, a passphrase, cookies, an encrypted key, a unique ID, a userID and password, and combinations thereof.

21. The computer system of claim 18, further comprising program instructions, stored on the one or more storage devices for execution by the one or more processors via the one or more memories, to:

determine an authorization level of the secure token in response to receiving validation of the secure token;

determine a required authorization level of the requested data files; and determine the authorization level of the secure token meets or exceeds the required authorization level of the requested data file, and in response to the determination, send the requested data file to the electronic device.

22. The computer system of claim 18, wherein the program instructions to receive the secure token from the electronic device are executed responsive to determining that the electronic device is not currently authorized to access the data file.

23. The computer system of claim 18, further comprising program instructions, stored on the one or more storage devices for execution by the one or more processors via the one or more memories, to send a message to a known user of the mobile device notifying the known user of the mobile device that the data file was requested.

24. The computer system of claim 18, further comprising, subsequent to receiving the data file on the mobile device, program instructions, stored on the one or more storage devices for execution by the one or more processors via the one or more memories, to determine whether the data file can be stored on the mobile device; and responsive to determining the data file can be stored on the mobile device, program instructions to store the data file.

* * * * *